United States Patent [19]
Lebing et al.

[11] Patent Number: 5,886,154
[45] Date of Patent: Mar. 23, 1999

[54] CHROMATOGRAPHIC METHOD FOR HIGH YIELD PURIFICATION AND VIRAL INACTIVATION OF ANTIBODIES

[76] Inventors: Wytold R. Lebing, 1304 Pine Trail, Clayton, N.C. 27520-9324; Patricia Alred, 9890 Washington Blvd. Apt. 404, Gaithersberg, Md. 20878; Doug C. Lee, 116 Altair Cir., Apex, N.C. 27502; Hanns-Ingolf Paul, 1107 Queenferry Rd., Cary, N.C. 27511

[21] Appl. No.: 879,362

[22] Filed: Jun. 20, 1997

[51] Int. Cl.$^6$ .............................. C07K 1/36; C07K 16/00
[52] U.S. Cl. .................................. 530/390.1; 530/390.5; 530/388.1; 530/387.1
[58] Field of Search .............................. 862/389.1, 389.4, 862/380, 363, 387.1, 390.1, 416, 418, 364, 390.5, 388.1

[56] References Cited

U.S. PATENT DOCUMENTS

| | | | |
|---|---|---|---|
| 4,939,176 | 7/1990 | Seng | 514/724 |
| 4,983,722 | 1/1991 | Bloom et al. | 530/387 |
| 5,164,487 | 11/1992 | Kothe | 530/389.1 |

FOREIGN PATENT DOCUMENTS

| | | | |
|---|---|---|---|
| 1201063 | 2/1986 | Canada | A61K 39/395 |

OTHER PUBLICATIONS

McKinney, M (1987) Journal of Immunological Methods, vol. 96 pp. 271–278.

*Primary Examiner*—Mary E. Mosher
*Assistant Examiner*—Rebecca A. Fuldner
*Attorney, Agent, or Firm*—Michael J. Beck; James A. Giblin

[57] ABSTRACT

An improved process for the purification of antibodies from human plasma or other sources is disclosed. The process involves suspension of the antibodies at pH 3.8 to 4.5 followed by addition of caprylic acid and a pH shift to pH 5.0 to 5.2. A precipitate of contaminating proteins, lipids and caprylate forms and is removed, while the majority of the antibodies remain in solution. Sodium caprylate is again added to a final concentration of not less than about 15 mM. This solution is incubated for 1 hour at 25° C. to effect viral inactivation. A precipitate (mainly caprylate) is removed and the clear solution is diluted with purified water to reduce ionic strength. Anion exchange chromatography using two different resins is utilized to obtain an exceptionally pure IgG with subclass distribution similar to the starting distribution. The method maximizes yield and produces a gamma globulin with greater than 99% purity.

6 Claims, 2 Drawing Sheets

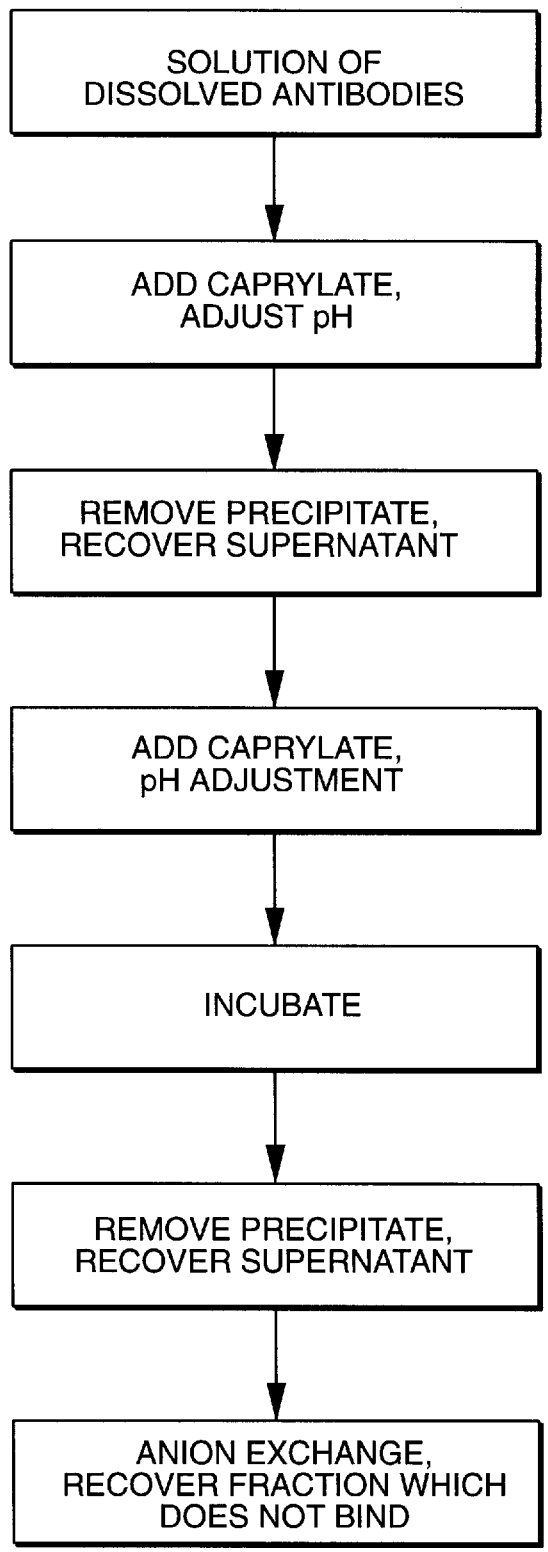
FIG._1

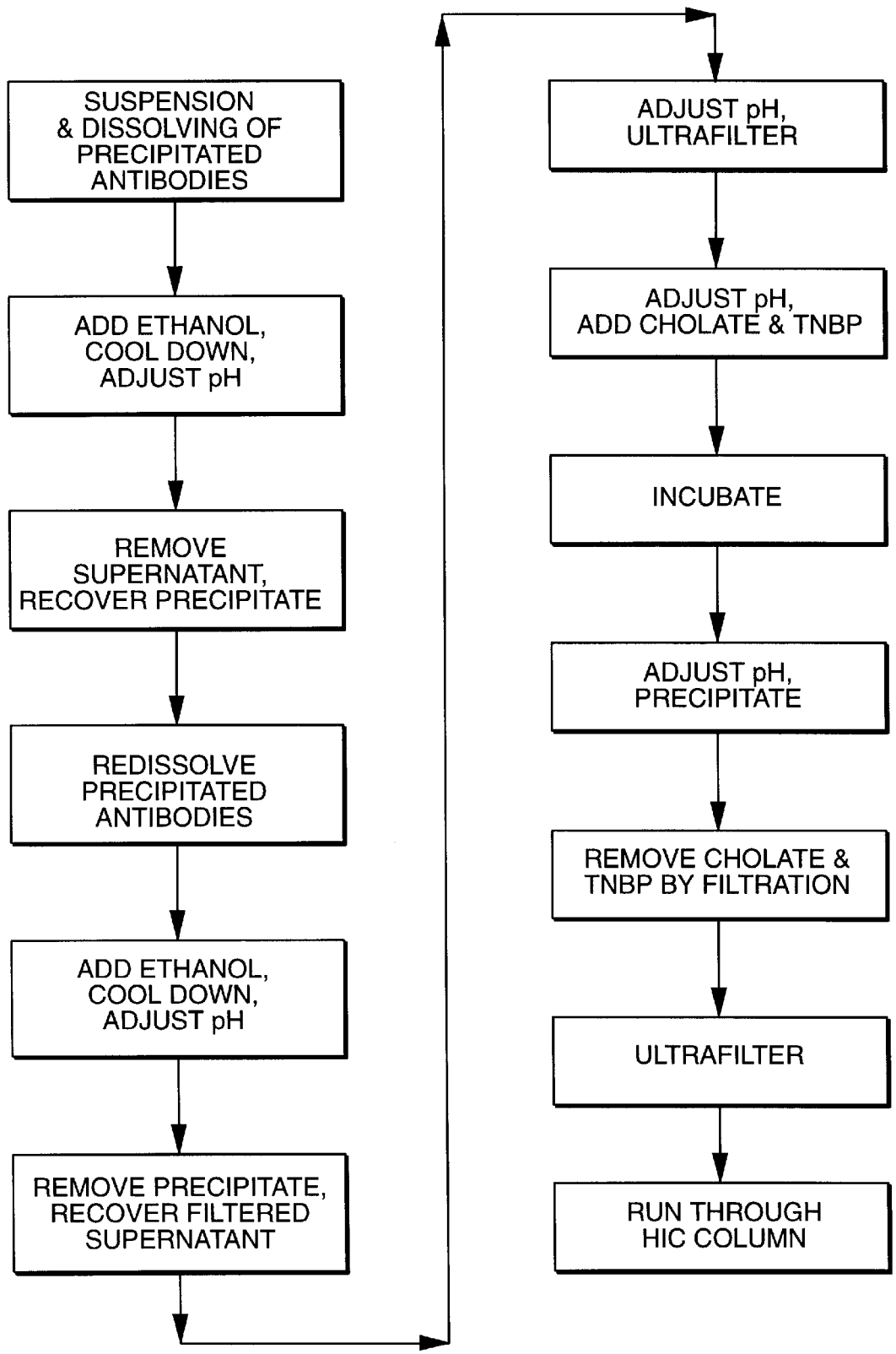
FIG._2
(PRIOR ART)

CHROMATOGRAPHIC METHOD FOR HIGH YIELD PURIFICATION AND VIRAL INACTIVATION OF ANTIBODIES

BACKGROUND OF THE INVENTION

1. Field

This disclosure is generally concerned with protein purification and virus inactivation/removal and specifically with an improved process for the purification of gamma globulins from blood plasma and other sources.

2. Background

Carboxylic acids such as caprylic acid have been used in both preparation of plasma products (precipitation of proteins) and inactivation of viruses. See, for example, the summary of such use in Seng et al. (1990).

Fractionation using caprylate:

During human immunoglobulin preparation caprylic acid is generally recognized as an effective precipitating agent for most plasma proteins at pH 4.8, so long as parameters such as temperature and ionic strength are optimized. Steinbuch et al. (1969) have described the precipitation of the bulk of the plasma proteins with caprylic acid without affecting IgG, ceruloplasmin and IgA. Steinbuch et al. isolated IgG from mammalian sera using caprylic acid and reported that extensive non-immunoglobulin precipitation was best obtained at slightly acidic pH, but not below pH 4.5. Plasma was diluted 2:1 with 0.06M acetate buffer, pH 4.8, and then treated with 2.5 wt. % caprylate to initiate precipitation. Batch adsorption of the supernatant on DEAE-cellulose was used to clear additional impurities from the isolated IgG fraction. Later work by Steinbuch et al. showed the use of caprylic acid to precipitate most proteins and lipoproteins (other than the immunoglobulins) present in Cohn ethanol Fraction III. (Steinbuch et al., 1973).

The method of Steinbuch, supra, was applied to cell culture medium and ascites fluid from mice, using 0.86 wt. % caprylic acid for recovery of IgG. (Russo et al., 1983). The same method was applied to diluted human plasma using 2.16 wt. % caprylate. (Habeeb et al., 1984). Habeeb et al. followed the caprylic acid precipitation with fractionation on DEAE cellulose. The resulting plasma-derived IgG was free of aggregates, plasmin and plasminogen. In addition, the IgG obtained was low in anticomplement activity and relatively stable during storage.

As a result of these studies, scientists further developed several techniques for purifying IgA, IgG, alpha-1 acid glycoprotein, and prealbumin, concluding concurrently that the precipitation reaction was highly temperature and pH dependent. (Steinbuch et al., 1969; Steinbuch et al., 1973; see also Tenold, 1996).

As an example, IgA has been prepared as a routine fractionation by-product from Cohn fraction III, based on IgA solubility with caprylic acid present at pH 4.8. (Pejaudier et al., 1972). IgA isolated from cold ethanol Fraction III by DEAE-cellulose adsorption and elution was further purified by caprylic acid precipitation. Conditions for precipitation were 1.5–2% protein concentration, 0.9% sodium chloride, pH 5.0, 1.12 wt. % caprylic acid.

A two step purification of immunoglobulins from mammalian sera and ascites fluid has been described (McKinney et al., 1987). First albumin and other non-IgG proteins were precipitated using caprylic acid, and then ammonium sulfate was added to the supernatant to precipitate the IgG.

U.S. Pat. No. 5,164,487 to Kothe et al. (1992) concerns the use of caprylic acid for the manufacture of an intravenously tolerable IgG preparation free from aggregates, vasoactive substances and proteolytic enzymes. The method includes contacting the starting material containing IgG with 0.4% to 1.5% caprylic acid before chromatographic purification with an ion exchange or hydrophobic matrix.

Sodium caprylate has also been used to purify albumin. According to these methods, sodium caprylate is added to process plasma, and protects the albumin when the process stream is exposed to high temperatures. Extreme temperatures not only denature process stream globulins, but may also generate contaminant neo-antigens. (Schneider et al., 1979; Condie, 1979; see also Plan, 1976).

Tenold (1996) shows the use of caprylate as a partitioning agent for the isolation of albumin from Cohn fraction II+III or IV-1 effluent. Again the sodium caprylate is used to denature (and precipitate) globulins.

Viral inactivation:

U.S. Pat. No. 4,939,176 to Seng et al. (1990) reports a process for inactivating viruses in solutions of biologically active proteins by contacting the solutions with caprylic acid. The preferred conditions recited for the process were pH 4 to pH 8, and 0.07% to 0.001% of the non-ionized form of caprylic acid.

Other methods of viral inactivation through the use of chemical agents are known. U.S. Pat. No. 4,540,573 to Neurath (1985) teaches the use of di- or tri-alkyl phosphates as antiviral agents. U.S. Pat. No. 4,534,972 to Lembach (1985) describes a method of rendering solutions of therapeutically or immunologically active proteins substantially free of infectious agents. In Lembach's method a solution of protein is contacted with a transition metal complex, e.g. copper phenanthroline, and a reducing agent to effect inactivation of viruses without substantially affecting the activity of the protein.

Anion exchange chromatography:

Bloom et al. (1991) gives an example of the use of anion exchange chromatography to purify antibody preparations. Their method includes contacting a solution containing antibodies and contaminating protein A with an anion exchange resin and then eluting the antibodies from the resin under conditions of increasing ionic strength.

Canadian Patent 1,201,063 to Friesen teaches the preparation of an IgG suitable for intravenous use by subjecting a plasma fraction to a two stage separation process using two different anion exchange resins. In each stage the buffer that is used to equilibrate the anion exchange resin is also used to elute the IgG containing fraction from the resin.

A method of isolating a human IgG and albumin containing composition for intravenous administration has been described by Kimura et al. (1984). The method involves precipitation steps under controlled conditions of pH, ethanol concentration, ionic strength and temperature.

SUMMARY OF THE INVENTION

The invention is an improved process for the purification of antibodies (especially of the IgG type) from human plasma and other sources. The process involves suspension of the antibodies at pH 3.8 to 4.5 followed by addition of caprylic acid (or other source of caprylate) and a pH shift to pH 5.0 to 5.2. A precipitate of contaminating proteins, lipids and caprylate forms and is removed, while the majority of the antibodies remain in solution. Sodium caprylate is again added to a final concentration of not less than about 15 mM. This solution is incubated under conditions sufficient to substantially reduce the titer of active virus (e.g., for 1 hour at 25° C.). A precipitate (mainly caprylate) is removed and the clear solution is diluted with purified water to reduce ionic strength. Anion exchange chromatography using two different resins is utilized to obtain an exceptionally pure antibody preparation with antibody subclass distribution similar to the starting distribution.

This method differs from the prior art since it combines virus inactivation and removal as an integral part of the processing scheme and minimizes post virus treatment manipulation of the gamma globulin solution. By integrating virus treatment into the processing scheme, the method maximizes yield and produces a gamma globulin with greater than 99% purity.

BRIEF DESCRIPTION OF THE FIGURES

FIG. 1 is a flow chart describing the process of the invention.

FIG. 2 is a flow chart showing the prior art process for isolating antibodies.

SPECIFIC EMBODIMENTS

Materials and Methods

Adjustments of pH were done with 1M acetic acid, 2M acetic acid, 6% NaOH, 1M NaOH, or 1M HCl. Sodium caprylate stock solution was made by dissolving 30% sodium caprylate in water for injection by mixing. Human plasma fraction II+III was produced as described by Lebing et al. (1994). All reagents were USP grade or better. Nephelometry was done using a Beckman Array 360 Nephelometer and Beckman kits. Analytical HPLC was done using HP 1050 systems with Tosohaas G3000SW and G4000SW SEC columns. Protein was determined using the Biuret method.

The procedure is robust and simple. (See FIG. 1.) The process begins by redissolving precipitated antibodies in purified water at a pH around 4.2. In practice, increasing the amount of water per unit of paste results in increased yield. However, when processing hundreds of kilograms of paste it is practical to sacrifice some yield in order to keep vessel and column scale within workable limits. Yields across the dissolving step, viral inactivation, and chromatography are relatively important since immunoglobulin demand generally far exceeds supply.

Inactivation of enveloped viruses requires that the bulk of the pH sensitive precipitate be removed prior to the inactivation step. In addition, sodium caprylate content should be 15–60 mM during the 25° C. hold to achieve complete inactivation of enveloped viruses. Virus inactivation studies have confirmed that caprylate at 16 mM or 18 mM inactivates over 4 log units of Bovine Viral Diarrhea Virus and Pseudorabies virus (both enveloped viruses) in 30 minutes at 24° C. This additional chemical virus inactivation supplements the virus inactvation of a pH 4.25 hold step also incorporated into the manufacturing process.

The primary steps of the process are defined as:

1) Suspending a composition containing precipitated immunoglobulins in purified water for injection (WFI) at 5° C. with vigorous mixing. In a preferred embodiment fraction II+III paste is used, but other sources may also be used, such as ascites fluid, tissue culture media containing antibodies, other human plasma fractions, or animal plasma fractions.

2) Dissolving immunoglobulins into solution by lowering the mixture to pH 3.8 to 4.5, preferably 4.2, by the addition of acid, preferably acetic acid, with further vigorous mixing.

3) Adding a source of caprylate ions (e.g., 40% w/v sodium caprylate in water) to a final concentration of 15 mM to 25 mM, preferably 20mM, and adjusting the pH up to 5.0 to 5.2, preferably 5.1, with a base (such as 1M NaOH).

4) Removal of precipitated proteins, lipids, and caprylate by filtration at ambient temperature (e.g., 5°–25° C.). The filtration requires addition of filter aid (for example, in this case the filter aid is 2% to 5% diatomaceous earth). The solution is filtered using normal flow filtration. This step results in significant reduction of non-enveloped virus. Centrifugation may be substituted for filtration.

5) Addition of further caprylate to adjust the concentration back up to about 15 mM to about 60 mM, preferably 20 mM, while pH is held at 5.0–5.2, preferably 5.1, by the addition of acid (e.g. 1M acetic acid).

6) The temperature is increased to about 25°–35° C., preferably 25° C., and held for a period of about 15 minutes to about 6 hours, preferably about one hour. Longer incubation times may be used with some sacrifice in yield. A precipitate of principally caprylate and some additional protein is formed during this step.

7) Filter aid (diatomaceous earth) is added and precipitate is removed by normal flow filtration. Enveloped viruses are inactivated by the caprylate hold, and non-enveloped viruses are captured on the filter pad.

8) The clarified solution is diluted with purified water to reduce conductivity between 1–8 mS/cm, preferably less than 5 mS/cm.

9) Passing the solution through two anion exchange chromatography columns linked in series. The anion exchangers are chosen for ability to remove IgA, IgM, albumin and other remaining protein impurities. After loading, the columns are washed with equilibration buffer. The flow through and wash fraction are collected as purified IgG. Both columns are equilibrated with the same buffer and at the same pH.

Several anion exchange resin combinations may be utilized depending on selectivity of the resins. The anion exchange resins are chosen for their ability to selectively remove the impurities found in alcohol/pH precipitated plasma fractions. In developing this method satisfactory purifications were obtained with combinations of Pharmacia Biotech Q & ANX resins and E. Merck TMAE Fractogel.

Conditions described for the chromatography generally range from pH 5.0 to 5.2. At pH<5.0 impurities pass through the columns. At pH>5.2 yield is sacrificed. Ionic strength during the chromatography is relatively important since reduced purity is observed as ionic strength is increased during the chromatography.

In preferred embodiments, the solution is applied directly to the first anion exchanger which has been equilibrated with 20 mM sodium acetate at pH 5.1. This is followed by applying the non-binding fraction (the flow through) from the first anion exchange column directly onto the second anion exchange column. This column has also been equilibrated with 20 mM acetate buffer at pH 5.1. The protein solution is typically loaded onto the first column at a ratio of 50–110 mg IgG/ml packed resin. The protein solution is typically loaded onto the second column at a ratio of 75–95 mg IgG/ml packed resin. The protein to resin ratios can also be adjusted beyond these limits, but doing so will have an impact on yield and purity. The protein solution is followed by approximately 2 column volumes of the equilibration buffer, which washes any non-bound IgG off of the columns. The unbound fraction is collected as highly purified IgG, which is then diafiltered and the protein is concentrated to final formulation values.

The preferred conditions for final product are chosen based on patents held by this manufacturer. These conditions (low pH and low salt) would, in theory, benefit any IgG product. The collected protein is adjusted to pH 4.2. It is ultrafiltered to a concentration of approximately 5% (w/v). It is then diafiltered with purified water.

The purified IgG is either concentrated to a stable liquid formulation (as described by Tenold, 1983) or other appropriate final formulation (e.g. a freeze dried formulation). For a liquid formulation the purified IgG is concentrated to yield either 5% or 10% IgG (w/v) following sterile filtration. Prior to filtration, the pH is adjusted to 3.80 to 4.25 and maltose or glycine is added to adjust osmolarity to be compatible for intravenous injection. The sterile bulk is then held for not less than 21 days to reduce anti-complement activity and to inactivate enveloped viruses.

As used herein, percent values for concentrations are determined on a weight/volume basis.

As used herein, to substantially reduce the titer of active virus means to reduce the titer of active virus by at least about 2 log units, more preferably at least about 3 log units, and most preferably at least about 4 log units.

As used herein, substantially all of a protein means at least about 90% of the protein. Substantially none of a protein means less than about 5% of the protein.

EXAMPLE 1

Purification of IgG from Cohn fraction II+III paste

Fraction II+III paste was solubilized in 12 volumes of 5° C. purified water. The mixture pH was adjusted to pH 4.2 with acetic acid, and mixed for 1 hour. This step put the IgG into solution.

The mixture pH was then adjusted up to pH 5.2 with NaOH and sodium caprylate (the "pH swing"). Proteins and lipids were precipitated. The mixture was clarified by filtration to remove precipitate which would interfere with virus inactivation. The caprylate concentration was adjusted to 20 mM at pH 5.1, and the mixture was incubated for 1 hour at 25° C. to effect enveloped virus inactivation.

The mixture was filtered to produce a clear solution for chromatography. The solution conductivity was adjusted to between 2.0 and 3.0 mS/cm using purified water. The pH of the solution was adjusted to 5.0 to 5.2 following the conductivity adjustment.

The solution was then applied directly to two anion exchange columns (a strong anion exchanger followed by a weak anion exchanger). The two columns were linked in series. The IgG flowed through the column while impurities (including the caprylate) were bound to the two anion columns.

The pH of the collected flow through from the chromatography was adjusted to 3.8 to 4.0 using acetic acid. It was diafiltered with seven exchanges of buffer (purified water). It was then concentrated and final formulated at pH 4.2.

The overall yield from paste dissolving to final product was 69% (see the table). This was a significant improvement over the prior process yield using the alcohol process wash (48%). (See FIG. 2, which outlines the prior process.)

TABLE

Yield Summary

| Process | Starting Amount | Recovery g/liter plasma | Recovery % Process |
|---|---|---|---|
| New Chromatography Process | 7.0 kg | | |
| Starting II + III paste | | 6.5 | |
| Post CIM Treatment | | 5.45 | 84% |
| Post Chromatography | | 5.0 | 77% |
| Final Container | | 4.5 | 69% |
| Old Production Process | 7.0 kg | | |
| Starting II + III paste | | 6.5 | |
| Effluent III | | | |
| Filtrate III | | | |
| Final Container | | 3.1 | 48% |

EXAMPLE 2

Purification of IgG from cell culture medium

Cell line growth media containing secreted monoclonal antibodies is first adjusted to the proper pH and conductivity. This accomplished by diafiltering against purified water while adjusting the pH to 4.2 with acetic acid. The conductivity should be less than 1.0 mS.

Purification of the monoclonal antibody is achieved by following the steps above. The purified monoclonal antibody is then concentrated and final formulated to a pH of 4.2 using glycine, maltose, or other suitable excipients. By formulating at pH 4.2 a liquid solution stable for 2 years at 5° C. can be achieved. This is highly desirable from a commercial standpoint.

DISCUSSION

Immunoglobulins precipitate with the II+III fraction during the Cohn alcohol fractionation. Precipitation relies on the overall charge of the protein surface and its interaction with the solvent. Exacting salt, alcohol, and pH ranges can somewhat limit the range at which proteins precipitate. However, most proteins precipitate across a wide range of pH and alcohol concentration (as much as 1.5 pH units and 10% alcohol). Thus precipitation ranges of proteins tend to overlap. All three major immunoglobulin types, IgG, IgA, and IgM, are coprecipitated due to the similarity of their isoelectric points. Further separation of the immunoglobulin is complicated by this similarity. Therefore, production schemes which utilize precipitation require that a significant amount of the IgG is coprecipitated with the IgA and IgM.

In addition to yield decrease, classical precipitation requires the use of ethanol. Since ethanol destabilizes the proteins, reduced temperatures (typically −5° C.) are required during processing to increase protein stability. Chromatography can avoid problems of protein denaturation that commonly arise in precipitation strategies. The protein chromatography steps generally can be done under conditions which favor protein stability. Another disadvantage of ethanol fractionation is that due to its chemical nature alcohol is a potential explosion hazard which requires explosion proof facilities and special handling protocols. This fact significantly increases the cost of the fractionation process, a drawback which does not exist with conventional chromatographic methods.

Ion exchange chromatography takes advantage of surface distribution and charge density on both the protein and the ion exchange media. The anion exchange resin presents a positively charged surface. The charge density is specific to the resin and generally is independent of pH (within the working range of the resin). A typical anion exchanger will bind proteins which have a net negative charge (i.e. when the pH of the solution is above the isoelectric point of the protein). In reality, the surface of a protein does not present a singular charge; rather it is a mosaic of positive, negative, and neutral charges. Surface structure is specific to a given protein and will be affected by solution conditions such as ionic strength and pH. This uniqueness can be exploited to establish specific conditions where individual proteins will bind or release from the anion exchange resin. By establishing these conditions, proteins with only slightly differing surface or charge properties can be effectively separated with high yield (>95%).

Improvements in the structure of chromatography resin supports have made large scale chromatography a practical alternative to more conventional purification methods. Rigid resins allow large volumes to be processed rapidly (<5 hours), and high ligand density gives the increased capacity necessary for large volume processing. These factors coupled with high yields, product purity and process simplicity favor the use of chromatography in large scale manufacturing.

CONCLUSION

The chromatography process described herein takes advantage of the high specificity of chromatography resins. Two anion exchangers are used to selectively remove protein contaminants and the viral inactivation agent. The resulting product is of >99% purity when assayed by either nephelometry or size exclusion chromatography (SEC-HPLC).

The process is also designed to minimize loss of IgG. Virus inactivation and removal has been carefully integrated into the dissolving and chromatography steps, therefore increasing the process efficiency. The overall yield from paste dissolving to final product is 69% (see the table). This is a significant improvement over the current process yield using the alcohol process wash (48%).

The process was performed on human Cohn fraction II+III paste in example 1. However, it is anticipated that the process may be used with equivalent results on plasma fractions isolated from non-human animals as well.

The above examples are intended to illustrate the invention and it is thought variations will occur to those skilled in the art. Accordingly, it is intended that the scope of the invention should be limited only by the claims below.

REFERENCES

Bloom, James W., et al., Removal of protein A from antibody preparations, U.S. Pat. No. 4,983,722 (Jan. 8, 1991).

Condie, Richard M., Preparation of intravenous human and animal gamma globulins and isolation of albumin, U.S. Pat. No. 4,136,094 (1979).

Friesen, Albert D., Process for preparing purified immune globulin (IgG), Canadian Patent 1,201,063 (1986).

Habeeb, A. F. S. A., et al., Preparation of human immunoglobulin by caprylic acid precipitation, Prep. Biochem. 14: 1–17 (1984).

Kimura, Tokosuke, et al., Method of preparing gamma globulin suitable for intravenous administration, U.S. Pat. No. 4,476,109 (1984).

Kothe, Norbert, et al., Manufacturing intravenous tolerable immunoglobulin-G preparation, U.S. Pat. No. 5,164,487 (1992).

Lebing, Wytold R., et al., A highly purified antithrombin III concentrate prepared from human plasma fraction IV-1 by affinity chromatography, Vox Sang. 67: 117–24 (1994).

Lembach, Kenneth J., Protein compositions substantially free from infectious agents, U.S. Pat. No. 4,534,972 (1985).

McKinney, Michella M., et al., A simple, non-chromatographic procedure to purify immunoglobulins from serum and ascites fluid, J. Immunol. Meth. 96: 271–78 (1987).

Neurath, Alexander R., et al., Undenatured virus-free biologically active protein derivatives, U.S. Pat. No. 4,540,573 (1985).

Pajaudier, L., et al., Preparation of human IgA as by-product of routine fractionation, Vox. Sang. 23: 165–75 (1972).

Plan, Robert A. M., et al., Process for the preparation of purified albumin by thermocoagulation and albumin obtained by said process, U.S. Pat. No. 3,992,367 (1976).

Russo, C., et al., Immunol. Meth. 65: 269–71 (1983).

Schneider, et al., Process for isolating albumin from the blood, U.S. Pat. No. 4,156,681 (1979).

Seng, Richard L., et al., Viral inactivation process, U.S. Pat. No. 4,939,176 (1990).

Steinbuch, M., et al., The isolation of IgG from mammalian sera with the aid of caprylic acid, Arch. Biochem. Biophys. 134: 279–94 (1969).

Steinbuch, M., et al., Preparation of an IgM and IgA enriched fraction for clinical use, Prep. Biochem. 3: 363–73 (1973).

Tenold, Robert, Intravenously injectable immune serum globulin, U.S. Pat. No. 4,396,608 (1983).

Tenold, Robert, Low temperature albumin fractionation using sodium caprylate as a partitioning agent, U.S. Pat. No. 5,561,115 (Oct. 1, 1996).

What is claimed is:

1. A method of preparing a purified, virally inactivated antibody preparation from a starting solution comprising antibodies and other substances at an initial pH, the method comprising the sequential steps a) through e) of
    a) adjusting the pH of the starting solution to be within a range of from about 3.8 to about 4.5 to form an intermediate solution comprising dissolved antibodies,
    b) adding a source of caprylate ions to the intermediate solution of step a) and adjusting the pH of the intermediate solution to be within a range of from about 5.0 to about 5.2 to form a precipitate and a supernatant solution comprising dissolved antibodies,
    c) incubating the supernatant solution under conditions of time, temperature, and caprylate ion concentration to inactivate substantially all enveloped viruses,
    d) contacting the supernatant solution with at least one ion exchange resin under conditions that allow binding of at least some of the other substances to the resin while not allowing binding of the antibodies to the resin, and
    e) collecting the antibodies, the method further comprising the non-sequential step f) of,
    f) separating the precipitate from the supernatant solution after at least one of steps b) or c) to result in a significant reduction of non-enveloped viruses.

2. The method of claim 1 wherein the starting solution comprises plasma-derived antibodies.

3. The method of claim 1 wherein the starting solution is obtained from a mammalian cell culture medium.

4. A method of preparing a purified, virally inactivated immunoglobulin preparation from a starting material comprising immunoglobulin and other substances, the method comprising the steps of a) adjusting the pH of the starting material to be within a range of from about 3.8 to about 4.5 to form an intermediate solution comprising dissolved immunoglobulin, b) adjusting the intermediate solution of step a) to conditions of pH, temperature, and caprylate concentration such that a first precipitate and a first supernatant comprising immunoglobulin are formed, wherein the conditions under which the first precipitate and first supernatant form comprise a pH within a range of from about 5.0 to about 5.2 and a caprylate concentration within a range of from about 15 mM to about 25 mM, c) separating the first supernatant from the first precipitate, d) incubating the first supernatant under conditions of time, pH, temperature, and caprylate concentration such that a second precipitate and a second supernatant comprising immunoglobulin are formed, wherein the conditions under which the second precipitate and second supernatant form comprise a pH within a range of about 5.0 to about 5.2 and a caprylate concentration within a range of about 15 mM to about 40 mM, e) separating the second supernatant from the second precipitate, f) contacting the second supernatant with a first anion exchange resin under conditions of pH and ionic strength such that substantially none of the immunoglobulin is bound to the first resin but other substances are bound to the first resin, g) separating a fraction containing substantially all of the immunoglobulin from the result of step f), h) contacting the fraction of step g) with a second anion exchange resin under conditions of pH and ionic strength such that substantially none of the immunoglobulin is bound to the second resin but other substances are bound to the second resin, and i) separating the purified, virally inactivated immunoglobulin preparation containing substantially all of the immunoglobulin from the result of step h).

5. The method of claim 4 wherein the immunoglobulin is immunoglobulin G.

6. The method of claim 4 wherein the immunoglobulin in the starting material is obtained from a source selected from the group consisting of human plasma fractions, non-human animal plasma fractions, and mammalian cell culture medium.

* * * * *